United States Patent [19]

Frot et al.

[11] Patent Number: 5,483,344
[45] Date of Patent: Jan. 9, 1996

[54] PROCESS AND APPARATUS FOR PERFORMING DIFFERENTIAL REFRACTIVE INDEX MEASUREMENTS USING INTERFERENCE OF MODULATED LIGHT BEAMS PASSING THROUGH REFERENCE AND TEST SAMPLES

[75] Inventors: Didier Frot, Choisy le Roi; Claude Beauducel, Henonville; Pierre Gonzalez, Rueil-Malmaison; François Couillard, Yerres, all of France

[73] Assignees: Institut Francais du Petrole, Rueil-Malmaison; Francois Couillard, Yerres, both of France

[21] Appl. No.: 256,206

[22] PCT Filed: Oct. 27, 1993

[86] PCT No.: PCT/FR93/01054

§ 371 Date: Aug. 19, 1994

§ 102(e) Date: Aug. 19, 1994

[87] PCT Pub. No.: WO94/10552

PCT Pub. Date: May 11, 1994

[30] Foreign Application Priority Data

Oct. 28, 1992 [FR] France ................... 92 12946

[51] Int. Cl.⁶ .......................... G01N 21/41; G01N 21/43
[52] U.S. Cl. .......................... 356/361; 356/128; 356/130; 356/365
[58] Field of Search .................. 356/361, 128, 356/130, 365, 351, 345

[56] References Cited

U.S. PATENT DOCUMENTS

| | | | |
|---|---|---|---|
| 3,472,598 | 10/1969 | Hossmann | 356/361 |
| 3,680,963 | 8/1972 | Edwards et al. | 356/361 |
| 4,289,403 | 9/1981 | Allington | 356/361 |
| 4,571,082 | 2/1986 | Downs | 356/361 |
| 4,690,562 | 9/1987 | Davies et al. | 356/361 |
| 4,787,746 | 11/1988 | Couillard | 356/361 |
| 5,073,024 | 12/1991 | Valette et al. | 356/361 |
| 5,168,325 | 12/1992 | Yoder-Short | 356/361 |

Primary Examiner—Frank Gonzalez
Assistant Examiner—Jason D. Eisenberg
Attorney, Agent, or Firm—Antonelli, Terry, Stout & Kraus

[57] ABSTRACT

The invention relates to the measurement of the difference between refractive indexes of two media, traversed by a light beam the beams produce an interference figure consisting of fringes having a displacement which is measured.

According to the invention, the displacement of the fringes of the interference figure is detected with a photosensitive device and a phase modulation is performed on at least one of the beams and the modulation is controlled in order to obtain a movement of the fringes of the interference figure.

24 Claims, 3 Drawing Sheets

PROCESS AND APPARATUS FOR PERFORMING DIFFERENTIAL REFRACTIVE INDEX MEASUREMENTS USING INTERFERENCE OF MODULATED LIGHT BEAMS PASSING THROUGH REFERENCE AND TEST SAMPLES

BACKGROUND OF THE INVENTION

1. Field of the Invention

The present invention relates to the field of high performance liquid chromatography which determines the composition of a liquid medium by means of its refractive index.

The invention also relates to a process for measuring the difference between the refractive indexes of two media traversed by a light beam.

More precisely, the invention relates to a phase modulation and an interference fringe differential refractometer.

The use of the present invention allows improvements in high performance liquid chromatographs, known as HPLC, to be achieved.

2. Description of the Prior Art

Most detectors in use in the in this field are photometers and refractometers but also for very specific applications, electrochemical, conductometric or other detectors may be used.

Photometers have the advantage of exhibiting a high sensitivity and a great stability. They may be used in the case in which the eluates to be detected absorb the light within the range of wavelengths between about 190 and 700 ηm. But these photometers have major drawbacks: they are not universal devices and, in a single analysis, there may be eluates which absorb the light at different wavelengths or which even practically do not absorb it, which has the disadvantage, notably in preparative chromatography, of letting impurities pass unnoticed.

Furthermore, in the case of preparative chromatography, the photometer is rapidly saturated at around an optical density of the order of 2.

By dividing for example by 10 the length of the optical path in the vessel, this drawback is decreased but still more sensitivity is lost.

The main advantage of refractometers is that they are practically universal. Most of the devices which are currently manufactured use a light beam deviated through a double prismatic circulating vessel. In these detectors, a light source casts a beam onto a double photodetector after passing successively through a diaphragm, possibly concentrating lenses, a rotating glass strip with parallel faces for adjusting the optical zero of the device, i.e. for balancing the light intensity lighting up the two photodetectors, a double prismatic vessel, one for the reference liquid and the other for the phase to be analyzed.

When the refractive index of the phase to be analyzed varies, the prismatic section of the two successive vessels is such that the beam deviates from one photodetector to the other, according to the sign of difference of the indexes between the two vessels. However, in some cases, notably in preparative chromatography, where high concentrations may be found in one of the two vessels, or if an elution gradient is created, the index variations may be such that the beam may deviate to the point of saturation of the device, which means that the deviated beam eventually only lights up one of the two cells. The chromatogram is thus clipped and several peaks with a common base may no longer be distinguished.

As it is the case for photometers, these drawbacks may be decreased by reducing the deviations, but here again at the expense of a sensitivity loss. Saturation is then avoided, but the smaller peaks, i.e. impurities, are no longer distinguished in preparative chromatography.

Whatever the effort the problem created by an elution gradient is always present.

A refractometric system with a monochromatic source has also been proposed, whose beam is divided to pass through two vessels in parallel, one containing a reference liquid and the other, the phase to be analyzed, then the two beams are reassembled to light up a photodetector. Interferences occur because of the variation of the optical path as a function of the index variation. One may consider that the sinusoid followed by the intensity is linear in the vicinity of the zero difference index, which gives an acceptable sensitivity but does not solve the problems of saturation and of use of a gradient, and, as in the previous cases, saturation is avoided to the detriment of sensitivity.

French patent FR-2,596,526 illustrates an example of a refractometric detector in which each of the vessels (reference and measuring vessel) operative independantly in an interferometry system with the two vessels being supplied with light through the same source.

According to this prior art, the photometric detection is performed by two independent photodetectors which each receive a light intensity which is a sinusoidal function of the difference of the refractive indexes between the reference vessel or air and the measuring vessel. An individual calibration of each of the photometers is thus necessary.

This optical system notably includes a piezoelectric element for vibrating a mirror in which part of the light beam coming from the source is reflected. However, the piezoelectric element may generate a certain measurement drift (linked to the temperature rise) in time. Besides, the motion of the mirror by the piezoelectric element is necessarily limited in frequency and/or in amplitude, which allows neither a wide measuring range nor a high measuring accuracy.

It is well-known, as disclosed in French patent 2,254,996, as disclosed in patent application DT 25 18 197 or as disclosed in U.S. Pat. No. 4,289,403, that the measurement of an optical path may simply be extracted during the measuring of the phase shift recorded between the signal delivered by a photodetector located in an interference figure and the modulation applied to only one of the beams of the interferometer. This measurement of the optical path gives, for a given test distance, the refractive index difference for a stable reference or, when the index is known and remains constant, the same measurement allows the test distance to be determined.

These various teachings agree that the interferometric device must be stable, as compact as possible, and symmetrical from the viewpoint of the path taken by each of the beams.

U.S. Pat. No. 4,289,403 confirms this observation since the object there of is a modulator of a new kind which minimizes the optical path difference for each of the two beams passing therethrough, even if the resulting modulation exhibits some non-linearities.

In the German Patent 2,518,197, a compensation applied to the modulator allows the phase shift amplitude to be obtained. This system provides a fast response in the analysis of the phase shifts generated by variations in a physical quantity. This patent clearly shows that a compensation, in terms of high voltage for a Pockels cell for example, applied to the modulator is no longer linear over a phase shift of the order of 2×180° (approximately 4λ) and that a compensation higher than this value would damage the modulator. The dynamics of the device is thus limited thereby.

SUMMARY OF THE INVENTION

The present invention advantageously provides a device capable of satisfying the needs of chromatographists.

This is notably the case in the gradient elution mode where the refractive index difference expressed in wavelength is most often of the order of several orders of magnitude times λ.

In the prior art cited above, it is necessary to use two photodetectors which must be identical, which requires an individual calibration and prevents measurement on absorbing systems on the wavelength used.

The object of the present invention is notably to avoid the drawbacks cited above by providing a system of simple design which includes a single detector.

The present invention notably allows sensitivity and saturation to be made compatible, especially for preparative chromatography, and it also enables an elution gradient to be used in analytic chromatography and in preparative chromatography.

To that effect, according to the invention, in an interference differential refractometer, each vessel (reference and measuring vessel) takes part, irrespective of one another, in a single interferogram supplied with light by a single source (laser for example).

Furthermore, the invention, by using a Pockels cell as a modulator, suitably arranged in the interferometer components, allows the two beams to follow exactly (in the sense of the crystal cell) the same optical path. This characteristic results from the modulator of the invention being arranged in the path of the initial beam, before it is divided into two beams.

Moreover, using a well-known modulator prevents non-linearity problems linked to the use of a modulator of a new design such as that disclosed for example in U.S. Pat. No. 4,289,403.

Furthermore, the refractometer according to the invention exhibits almost no measurement drift and a high stability in the interferences which are produced. The measuring accuracy is advantageously improved since no mechanical limit is imposed with no part being set into motion.

Finally, the measuring range is very wide or even unlimited due to the nature and the combination of the elements of the invention.

To that effect, in the interference differential refractometer according to the invention, each of the vessels is part of the same interferometric system. The photometric detection will preferably be performed by a single detector arranged in the single interference figure produced by the interferometer.

In the text hereafter, the term "interference figure" describes the two beams being combined at the same point in space to give rise to a sinusoidal contrast illumination profile, and the case in which two beams combined in a single beam produce a "solid color interference" system. The analysis of the displacement of the interference fringes (sinusoidal illumination profile) or of the polarization state of the beam resulting from the combination of the two beams (solid colour interferences) gives a signal which is proportional to the refractive index difference produced by each of the beams passing respectively through each of the vessels.

The optical processing of the reference branch is modulated at a modulation frequency FM, the associated photodetector receives a luminous intensity which is a sinusoidal function of frequency FM whose phase is proportional to its spatial position. The luminous intensity thus also depends on the refractive index difference between the reference and the measuring vessel.

More precisely, in such a system, the photodetector remains stationary, and receives a luminous intensity having a sinusoidal variation over time, of a frequency equal to FM and whose phase variation depends on the variation of the index difference between the reference vessel and the measuring vessel. Therefore, if a phase measurement between the signal coming from the photodetector and a stationary reference is available, it is possible to measure the refractive index difference between the two vessels. The refractive index may vary progressively even to a great extent, for example in gradient.

The present invention thus solves the problem of measuring dynamically and with the maximum sensitivity which is sought in high performance liquid chromatography.

The invention relates to a process for measuring the difference between refractive indexes of two media, each one being traversed by a light beam with the beams producing an "interference figure" whose displacement is measured.

In accordance with the invention, one of the polarization components of beam F is modified, a phase modulation is performed on at least one of the polarization components of beam F in order to obtain a movement of the fringes of the interference figure, which allows the relative difference of the refractive indexes of the two media (Cr, Cm) to be quantified.

According to the invention, a single photosensitive device is used to detect the movement of the fringes of the "interference figure". The device detects the amplitude and the direction of movement of the fringes of the interference figure.

A Pockels cell may be used to modulate the phase.

The object of the invention is to provide a differential refractometer usable notably in high performance liquid chromatography, which may include:

a coherent light source emitting a beam F, an optical divider for dividing the polarization of the beam F coming from said source, a first optical element for making the two coherent beams produced by the optical divider parallel, two vessels Cr, Cm, with one of them, Cr, containing a reference liquid, and the other, Cm, a liquid to be measured, with each one being traversed by one of the two beams coming from the first optical system, an optical set combining each of the two beams I and II coming from the vessels and allowing an interference figure to be created, and a photodetector associated with said interference figure.

According to the invention, the refractometer further includes a first birefringent optical medium placed in the beam F of the source, upstream from the optical divider, and for modifying one of the components of the polarization of the beam F, a second birefringent optical medium placed upstream from the interference figure, preferably in one of the beams coming from the divider, an electronic system (11–18) for modulating the phase of one of the components of the polarization applied to the birefringent optical medium 2, with the electronic system also allowing the analysis of the relative instantaneous phase between the modulation signal R applied to the birefringent medium 2 and the signal S measured at the terminals of the photodetector 9, which allows the relative difference of the refractive indexes of reference vessel Cr and of measuring vessel Cm to be quantified, and a computer system for processing the data coming from the electronic system.

The first birefringent medium may preferably be a Pockels cell.

According to an embodiment of the invention, the optical set combining each of the beams I and II coming from the vessels includes a lens for creating the interference figure in its focus.

The photodetector may advantageously consist of an optical fiber having one end arranged at the focal point of a converging lens, an end surface of the lens which receives the light beam being perpendicular to the optical axis of the refractometer with another end of the optical fiber being connected to a photodetector.

According to another embodiment of the invention, the optical set combining each of the beams I and II includes the second polarizing birefringent optical medium and a semi-transparent mirror for deflecting the beam.

This optical set may also include a reflecting element for reflecting each of the two beams I and II through one of the vessels (Cr, Cm), towards the first optical element, the optical divider, the semi-transparent and the second birefringent optical medium.

BRIEF DESCRIPTION OF THE DRAWINGS

Other features and advantages of the invention will be clear from reading the description hereafter, given by way of non limitative examples, with reference to the accompanying drawings in which:

FIG. 1A shows a grid located at the focal point;

FIG. 3 is a simplified diagram of the electronic part of the invention.

DESCRIPTION OF THE PREFERRED EMBODIMENTS

Figure 1:
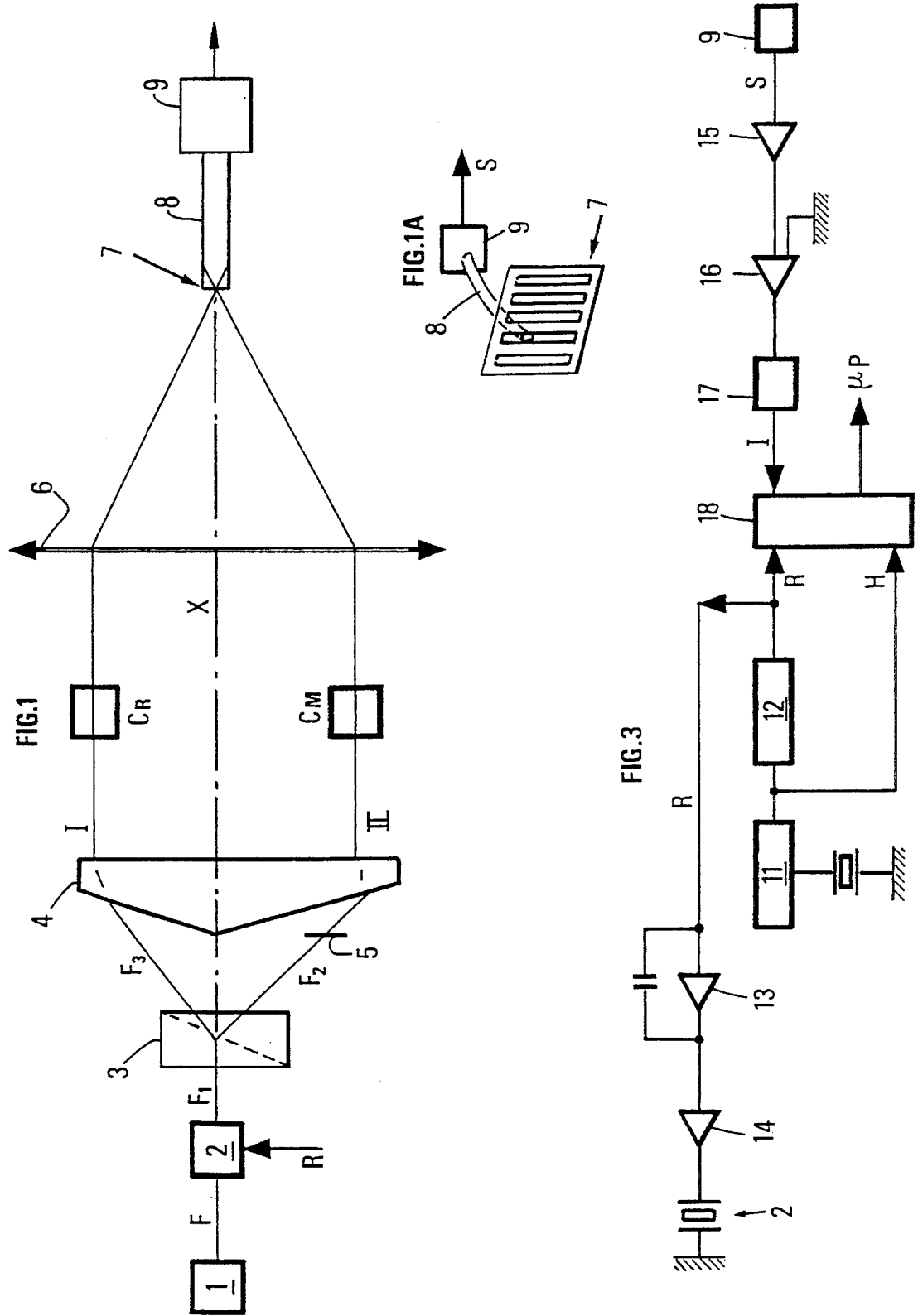
FIG. 1 is a diagram showing the main components of the invention and their mutual layout according to a first embodiment of the invention.

FIG. 1 diagrammatically illustrates the main components of the invention: a source 1 of coherent light, preferably monochromatic (of LASER type), emitting a polarized beam "F" consisting of two orthogonal components.

According to the invention, a Pockels cell 2 or any other birefringent optical medium known in the art is placed in the path of beam "F" and produces a phase lag or a phase lead, which generates at the cell output, a beam "F1" with one polarization component being is modified.

Furthermore, as explained hereafter, the Pockels cell 2 receives a modulation signal R coming from an electronic system. Using the Pockels cell as a modulator whose electric response is strictly capacitive, next to a piezoelectric wedge for example, provides a higher stability in the resultant interferences and much less drift during measuring.

Beam "F1" enters an optical divider 3 such as a Wollaston prism for example, for dividing it into at least two beams "F2" and "F3" which are sent into a first optical system 4. One of the beams is phase modulated, the other one is not.

The first optical element 4 may be, for example, a biprism or a converging lens which produces parallel and spatially spaced beams "F1" and "F2" which are not parallel at the output of divider 3.

A second birefringent optical medium 5 (or delay blade) is preferably placed in one of beams "F2" or "F3" in order to change the polarization of the optical beam (F2 for example) in which it is positioned, so that beams "F2" and "F3" enter the first optical element 4 (biprism) with the same polarization.

At the output of biprism 4, each of the two parallel beams I and II, with the same polarization state, spatially spaced apart, pass through a vessel Cm, containing the composition to be measured, and another vessel Cr containing a reference composition. The two vessels may actually be contained in a single block (or element).

After passing each through the vessels, beams I and II pass through a converging lens 6 which focuses the image of the two beams into a focal point 7. The interferences or interference "figure" 15 is created at the focal point 7.

An optimum contrast of the fringes forming the interference figure may be obtained by rotating the beam coming from light source 1 round its axis X.

An interference detector, located at focal point 7, may consist of an optical fiber 8 (of radius Rf) having one end positioned at the focal point 7 of the converging lens 6, so that radius Rf remains less than or equal to the distance between two interference fringes of equal nature and another end positioned to couple light passing through the optical fiber from the focal point to the photodetector 9. In other words, radius Rf has the same order of magnitude as the fringes.

The cross-section of optical fiber 8 is preferably perpendicular to the longitudinal axis X of the refractometer. This axis generally merges with the axis of light source 1. The other end of optical fiber 8 may be coupled to a linear photodetector 9 known in the art, working within a determined intensity range.

Without departing from the scope of the invention as illustrated in FIG. 1A, a grid located at focal point 7 on which the beams converge may directly be mechanically coupled to the same photodetector as illustrated in FIG. 1.

As it will be explained more in detail hereafter, the analysis of the relative instantaneous phase between the modulation signal applied to the Pockels cell 2 and the signal measured at the terminals of photodetector 9 will allow the relative refractive index difference between the reference vessel and the measuring vessel to be quantified.

Figure 2:
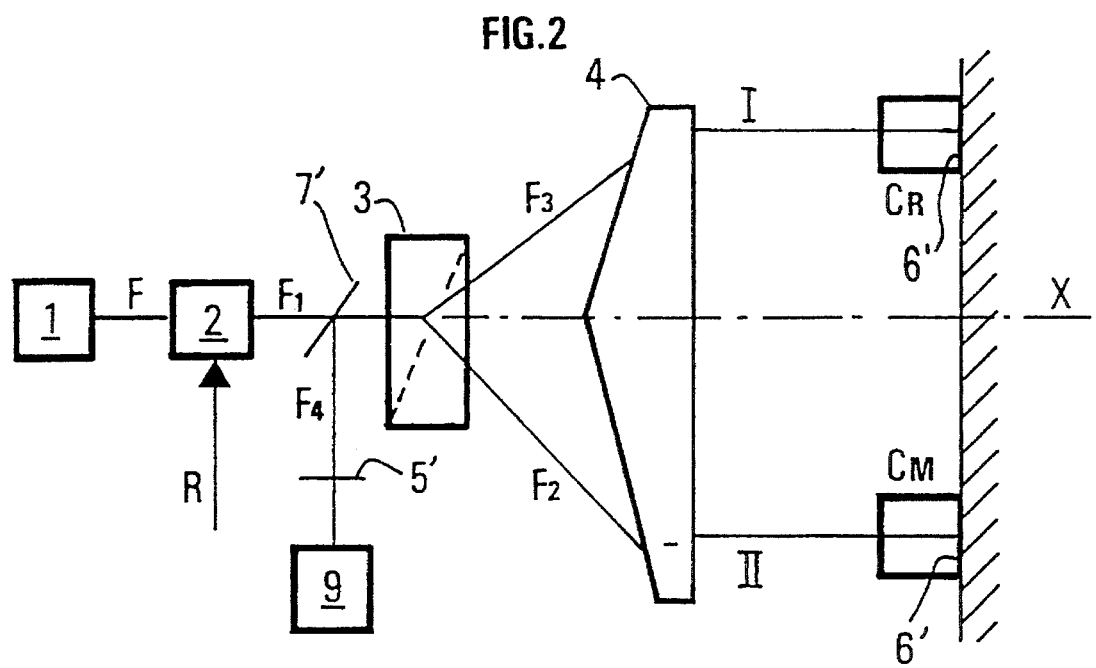
FIG. 2 is a diagram showing the main components of the invention according to another embodiment of the invention.

Another embodiment of the invention is described with reference to FIG. 2.

This embodiment is equivalent to the first embodiment as far as its functions and objectives. However, it required less costs and provides a higher sensitivity.

Only the differences between the first embodiment described above and the second embodiment will be stated:

After passing through modulator 2, beam "F1" intersects a semitransparent mirror 7' making preferably an angle of 45° with the principal axis X. Then beam "F1" enters an optical divider 3 such as a Wollaston prism for example for dividing it into at least two beams "F2" and "F3" which are optically coupled to a first optical system 4. One of the beams is phase modulated, the other is not.

As stated above, the first optical element 4 may be, for example, a biprism or a converging lens for making the two beams "F1" and "F2" parallel and spaced apart which are not parallel at the output of divider 3.

Thus, at the output of biprism 4, each one of the two parallel beams I and II are spatially separated respectively, pass through a vessel Cm containing the composition to be measured and another vessel Cr, containing a reference composition.

According to this embodiment of the invention, after passing each through the vessels beams I and II are reflected by a metallic layer 6' deposited on the rear face of each of the cells Cm, Cr. The beams I and II are reflected back to by biprism 4 and are recombined in divider 3 into a single beam F4 reflected at 90° from the principal axis X by means of semi-transparent mirror 7'.

Beam F4 passes through a polarizer 5' which allows the polarization state to be analyzed after recombination in divider 3. Beam F4 is then optically coupled to a photoreceptor 9.

Photoreceptor 9 receives a light beam intensity proportional to the projection of the amplitude of the electric field vector on the "transparent" axis of polarizer 5'.

Compared with the first embodiment of the invention, this other embodiment (interferometer folded) eliminates a half wave plate, a converging lens, an optical fiber or a slot system before the photoreceptor, The interferogram corresponding to the previous assembly is reflected back to a single interference order, so that the amplitude of the intensity at the terminals of photodetector 9 is highly increased, Because of the double passage (to-and-from) through each of the cells Cm and Cr, the system, with an equal vessel volume, becomes twice as sensitive, More generally, it is more compact (interferometer folded) and has a greater stability with respect to vibrations, expansions, etc.

As explained more in detail below, the analysis of the relative instantaneous phase between the modulation signal R applied to the Pockels cell 2 and the signal measured at the terminals of photodetector 9 allows the relative refractive index difference between the reference vessel and the measuring vessel to be quantified.

FIG. 3 shows a simplified diagram of the phase measurement principle which is of course valid for all the embodiments of the invention.

A quartz oscillator 11 provides a signal H having frequency equal to N times $F_m$ with N being the resolution of the phase measurement.

Signal H is divided by means of a divider 12 which delivers a reference signal $R_t$ of frequency $F_m$. This signal is transmitted to a reversible counter 18 and to the Pockels cell 2.

Before it is applied to the Pockels cell 2, signal R is preferably integrated in an integrator 13 and then amplified in an amplifier 14.

The signal S coming from photodetector 9 is preferably amplified in an amplifier 15, converted into a square wave signal of frequency ($2F_m$) and compared with a threshold value in a comparator 16. The signal is thereafter divided by 2 in a divider 17 to provide the interferometric measuring square signal I.

The rising front edge of signal I activates the counting start in reversible counter 18 counting at a frequency $N \times F_m$, while the rising front of the signal R applied to this counter 18 triggers the counting stop. The counter is then reset to zero until a new rising front comes from signal I.

Counter 18 (before zero reset) thus contains a number ($k_{fi}$) ranging between 0 and N, which represents the relative instantaneous phase between reference signal R and the measuring signal I coming from photodetector 9.

This number $k_{fi}$ may advantageously be transmitted to a data processing system (any microprocessor μP known in the art may be used) which computes the absolute instantaneous phase Φi every $1/F_m$.

Figure 4:
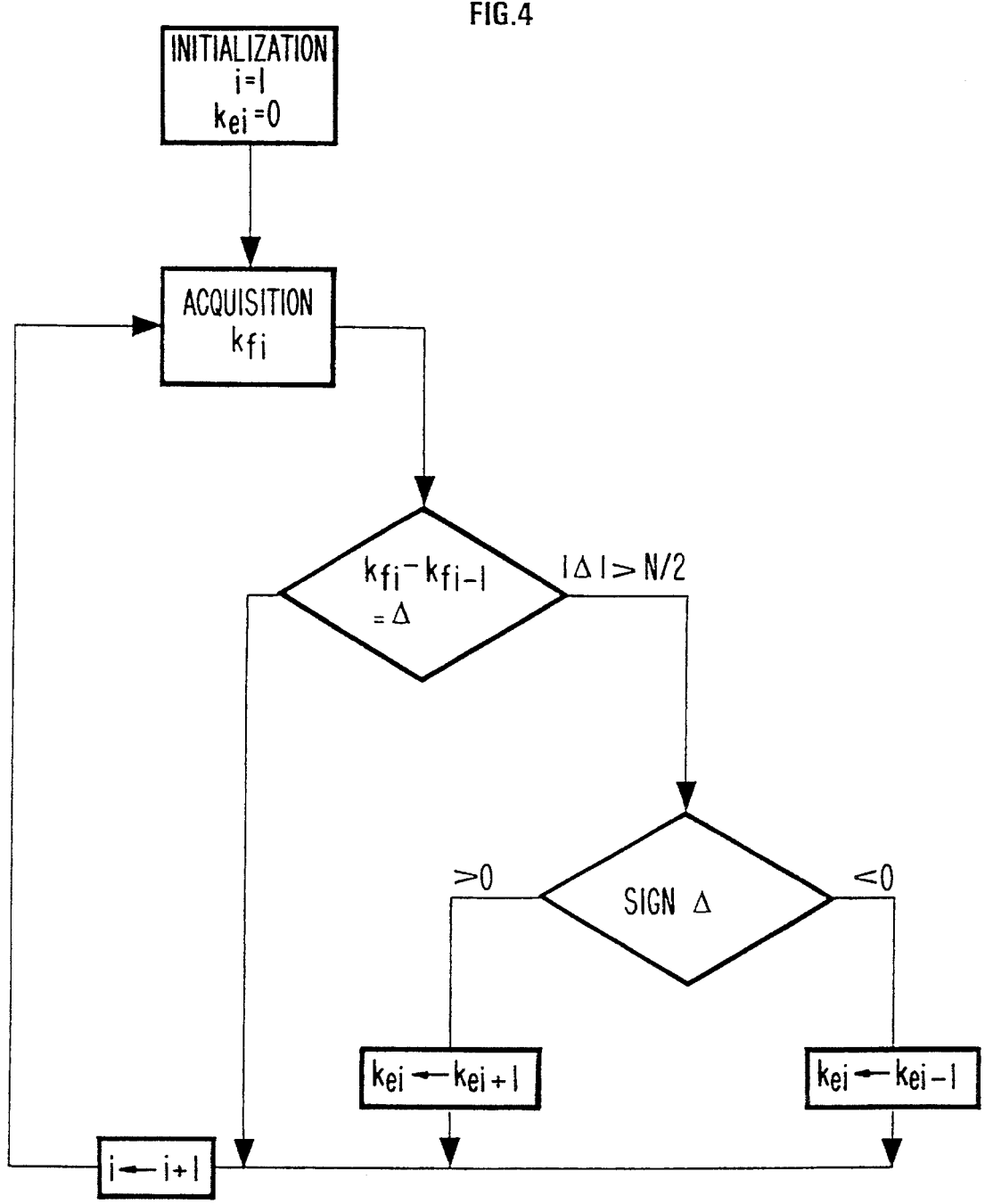
FIG. 4 illustrates a processing algorithm.

An example of a calculation algorithm is shown in FIG. 4. The calculated value $Φi=k_i \times 2π$ (in rd) with $k_i$ being a fractional value resulting from the concatenation of two microprocessor register values $k_{fi}$ and $k_{ei}$.

The absolute instantaneous phase Φi may be processed: average value, difference with respect to a threshold value, . . . in the microprocessor.

Several outputs may be provided, such as, for example, towards a microprocessor via an RS type computer link. An analog output may also be provided.

Furthermore, according to the invention, measurements may be successively carried out in two polarization configurations of the beams I and II passing through the vessels. Thus, according to a first measurement, the second birefringent optical element 5 is placed in beam "F2" whereas, according to a second measurement, element 5 is placed in beam "F3". A detection of the chiral nature of the molecules present in the measuring vessel may thus be achieved.

The invention is preferably used, as stated above for high performance liquid chromatography measurements, either in adsorption or in ion exchange for example.

The refractometer according to the invention may also be very advantageously utilized downstream from a gel-permeation chromatography column in view of its high measuring dynamics.

Besides, without major modification, the refractometer according to the invention is adaptable to the quantitative measurement of the refractive index of a solution as a function of the solute concentration: calibration measure necessary for operating the results obtained in static light scattering.

Of course, the refractometer described above may be utilized differently and/or modified by the man skilled in the art without departing from the scope of the present invention.

We claim:

1. A process for measuring a difference between refractive indices of a first reference media and a second test media comprising:

producing a coherent light beam;

modulating the coherent light beam in response to a reference signal to produce a modulated coherent light beam containing a modified polarization component;

dividing the modulated coherent light beam into spatially separated first and second coherent light beams and phase modulating one of the first and second beams;

passing the phase modulated coherent light beam through the first media and passing the second coherent light beam through the second media;

combining the first and second modulated coherent beams to produce an interference figure having fringes;

producing a time varying signal representing spatial displacement of the fringes of the interference figure; and measuring the difference between the refractive indices in response to a phase comparison of the reference and time varying signals.

2. A process in accordance with claim 1 wherein:

the modulated coherent light beam is produced with a Pockels cell which is controlled with a time varying modulation signal applied thereto.

3. A process in accordance with claim 2 wherein:

the detecting the movement of the fringes detects an amplitude and direction of displacement of the fringes.

4. A process in accordance with claim 1 wherein:

the detecting the movement of the fringes detects an amplitude and direction of displacement of the fringes.

5. A process in accordance with claim 1 wherein:

the refractive index of the second test media is measured as a function of solute concentration to calibrate a static light scattering device.

6. A differential refractometer for use in liquid chromatography comprising:

a coherent light source emitting a coherent light beam;

an optical divider, optically coupled to the coherent light beam, for dividing the coherent light beam into first and second coherent light beams;

a first optical element, optically coupled to the first and second coherent light beams, for outputting the first and second coherent light beams in parallel to each other;

a first vessel disposed within the first coherent light beam which contains a reference liquid which is traversed by the first coherent light beam;

a second vessel disposed within the second coherent light beam which contains the liquid to be tested which is traversed by the second coherent light beam;

a second optical element, optically coupled to the parallel first and second coherent light beams, for combining the parallel first and second coherent light beams to produce an interference figure;

a photodetector, optically coupled to the interference figure, for producing a time varying signal representing any time variation of the fringes;

a first birefringent optical medium placed in the coherent light beam upstream of the optical divider for modifying a component of polarization of the coherent light beam in accordance with a time varying reference modulation signal applied to the first birefringent optical medium;

a second birefringent optical medium coupled to at least one of the first and second coherent light beams or the interference figure for producing a time varying signal; and an analyzing system, coupled to the reference modulation signal and the time varying signal, for detecting a relative phase difference between the time varying reference modulation signal and the time varying signal and processing the relative phase difference to determine a relative refractive index difference between the reference liquid and the liquid to be tested.

7. A differential refractometer in accordance with claim 6 wherein:

the first birefringent medium is a Pockels cell.

8. A differential refractometer in accordance with claim 7 wherein:

the second optical element comprises a lens.

9. A differential refractometer as recited in claim 8 wherein:

the second birefringent optical medium is placed in one of the first and second coherent light beams downstream from the optical divider.

10. A differential refractometer as recited in claim 8 wherein:

the second optical element comprises a converging lens and an optical fiber having a first end surface perpendicular to an optical axis of the differential refractometer positioned at a focal point of the converging lens with a second end surface of the optical fiber coupled to the photodetector.

11. A differential refractometer as recited in claim 7 wherein:

the second birefringent optical medium is placed in one of the first and second coherent light beams downstream from the optical divider.

12. A differential refractometer as recited in claim 7 wherein:

the second optical element comprises a converging lens and an optical fiber having a first end surface perpendicular to an optical axis of the differential refractometer positioned at a focal point of the converging lens with a second end surface of the optical fiber coupled to the photodetector.

13. A differential refractometer in accordance with claim 6 wherein:

the second optical element comprises a lens.

14. A differential refractometer as recited in claim 13 wherein:

the second birefringent optical medium is placed in one of the first and second coherent light beams downstream from the optical divider.

15. A differential refractometer as recited in claim 13 wherein:

the second optical element comprises a converging lens and an optical fiber having a first end surface perpendicular to an optical axis of the differential refractometer positioned at a focal point of the converging lens with a second end surface of the optical fiber coupled to the photodetector.

16. A differential refractometer as recited in claim 6 wherein:

the second birefringent optical medium is placed in one of the first and second coherent light beams downstream from the optical divider.

17. A differential refractometer as recited in claim 16 wherein:

the second optical element comprises a converging lens and an optical fiber having a first end surface perpendicular to an optical axis of the differential refractometer positioned at a focal point of the converging lens with a second end surface of the optical fiber coupled to the photodetector.

18. A differential refractometer as recited in claim 6 wherein:

the second optical element comprises a converging lens and an optical fiber having a first end surface perpendicular to an optical axis of the differential refractometer positioned at a focal point of the converging lens with a second end surface of the optical fiber coupled to the photodetector.

19. A differential refractometer as recited in claim 6 further comprising:

a semitransparent mirror, disposed between the first birefringent optical medium and the optical divider, through which passes in a first direction the coherent light beam having a component of polarization modified by the first birefringent optical medium and which reflects in a third direction the interference figure with time varying fringes passing in the second direction from the second optical element to the semitransparent mirror; and wherein the first optical element and the second optical element are a single optical element and the second birefringent element is disposed in an optical axis of the differential refractometer extending in the third direction between the semitransparent mirror and the photodetector.

20. A differential refractometer in accordance with claim 19 wherein:

the coherent light source is a monochromatic laser.

21. In a process for measuring a difference between refractive indices of a first reference media and a second test media the improvement comprising:

producing a coherent light beam;

passing the coherent light beam through a birefringent optical element to modulate the coherent light beam;

passing the modulated coherent light beam through an optical divider to produce first and second coherent light beams;

passing the first and second coherent light beams respectively through the first and second media; and measuring the difference between the refractive indices of the first and second media in response to processing of the first and second modulated coherent light beams.

22. A process in accordance with claim 21 wherein:

the refractive index of the second test media is measured as a function of solute concentration to calibrate a static light scattering device.

23. A differential refractometer for use in liquid chromatography comprising:

a coherent light source for emitting a coherent light beam;

an optical divider, optically coupled to the coherent light beam, for dividing the coherent light beam into first and second coherent light beams;

a birefringent optical medium, placed in the coherent light beam upstream of the optical divider, for modifying a component of polarization of the coherent light beam;

a first vessel disposed within the first coherent light beam which contains a reference media which is traversed by the first coherent light beam;

a second vessel disposed within the second coherent light beam which contains a liquid to be tested which is traversed by the second coherent light beam;

an optical element, optically coupled to the first and second coherent light beams after passage respectively through the media, for combing the first and second coherent light beams into an interference figure; and a photodetector, optically coupled to the interference figure, for producing a time varying signal representing variation of the interference figure.

24. A differential refractometer for use in liquid chromatography in accordance with claim 23 further comprising:

at least one other birefringent optical medium, each of the at least one other optical birefringent medium being placed in a single one of the first and second coherent light beams upstream of the interference figure.

* * * * *